US005284768A

United States Patent [19]

Legoux et al.

[11] Patent Number: 5,284,768
[45] Date of Patent: Feb. 8, 1994

[54] SIGNAL PEPTIDE, DNA SEQUENCES CODING FOR THE LATTER, EXPRESSION VECTORS CARRYING ONE OF THESE SEQUENCES, GRAM-NEGATIVE BACTERIA TRANSFORMED BY THESE VECTORS, AND PROCESS FOR THE PERIPLASMIC PRODUCTION OF A POLYPEPTIDE

[75] Inventors: Richard Legoux, Caraman; Pascal Leplatois, Cuq Toulza; Evelyne Joseph-Liauzun, Saint Orens de Gameville; Gérard Loison, Toulouse, Willem Roskam, deceased, late of Montgiscard, France, by Nicol Brunt, Montgiscard, France, Legal Representative, all of France

[73] Assignee: Sanofi, Paris, France

[21] Appl. No.: 825,080

[22] Filed: Jan. 24, 1992

Related U.S. Application Data

[63] Continuation of Ser. No. 397,788, Aug. 24, 1989, abandoned.

[30] Foreign Application Priority Data

Aug. 24, 1988 [FR] France ................................ 88 11188

[51] Int. Cl.⁵ ................... C12N 15/09; C12N 15/70; C12N 1/21
[52] U.S. Cl. ........................ 435/252.33; 435/69.1; 435/69.8; 435/71.2; 435/172.3; 435/252.3; 435/320.1; 536/23.1; 935/48
[58] Field of Search .................. 435/69.1, 69.8, 71.2, 435/252.3, 252.33, 320.1, 172.3; 536/23.1

[56] References Cited

U.S. PATENT DOCUMENTS 4,565,785  1/1986  Gilbert et al. ...................... 935/48
4,711,844  12/1987  Chang .............................. 935/47

FOREIGN PATENT DOCUMENTS 0245138  11/1987  European Pat. Off. ...... C12N 15/00
0273800   7/1988  European Pat. Off. ...... C12N 15/00

OTHER PUBLICATIONS

Gascuel et al. (1986) J. Mol. Evol., vol. 24, pp. 130–142.
Talmadge et al. (1980), P.N.A.S., vol. 77 (6) pp. 3369–3373.
Dodt et al. (1986), FEBS Letters, vol. 202 (2) pp. 373–377.

Primary Examiner—Richard A. Schwartz
Assistant Examiner—J. LeGuyader
Attorney, Agent, or Firm—Foley & Lardner

[57] ABSTRACT

The invention relates to a signal peptide of the formula:

MXKSTLLLLFLLLCLPSWNAGA and X represents a direct bond between M and K, an amino acid selected from the group comprising the 20 amino acids of the genetic code, or a peptide containing 2, 3 or 4 amino acids selected, each independently of the other, from the group comprising the 20 amino acids of the genetic code.

10 Claims, 5 Drawing Sheets

Plasmid p 163,1

Plasmid p 160.1

Plasmid p 380.1
Plasmid p 373.2

Plasmid p 400.18

Plasmid p 460

SIGNAL PEPTIDE, DNA SEQUENCES CODING FOR THE LATTER, EXPRESSION VECTORS CARRYING ONE OF THESE SEQUENCES, GRAM-NEGATIVE BACTERIA TRANSFORMED BY THESE VECTORS, AND PROCESS FOR THE PERIPLASMIC PRODUCTION OF A POLYPEPTIDE

This application is a continuation of application Ser. No. 07/397,788, filed Aug. 24, 1989, now abandoned.

BACKGROUND OF THE INVENTION

The present invention relates to a novel signal peptide, to the DNA sequences coding for the latter, to the expression vectors carrying one of these sequences, to the Gram-negative bacteria transformed by these vectors and to a process for the periplasmic production of a polypeptide with the aid of these bacteria.

It is known that Gram-negative bacteria naturally produce polypeptides synthesized in the form of a precursor in the cytoplasm and exported towards the periplasm—the space between the cytoplasmic membrane and the bacterial wall—where they accumulate in the form of a mature polypeptide, i.e. a polypeptide which is capable of ensuring its specific biological action. These polypeptides include enzymes in particular, such as alkaline phosphatase.

It is also known that Gram-negative bacteria can be made to produce, in their periplasm, a polypeptide which is foreign to them. This kind of periplasmic production is of definite interest because it is easier to separate said polypeptide from the other constituents of the periplasm than to separate the polypeptide from the other components of the cytoplasm, as is required in the case of a production with accumulation in the cytoplasm. It is also of interest because the polypeptide accumulates in its mature form without the addition of an N-terminal methionine, which would then have to be removed, and without the adoption of an unfavorable secondary conformation.

It is known that, for its production to be periplasmic, a polypeptide must be synthesized in the form of a precursor corresponding to the mature polypeptide extended at its N-terminal end by a peptide, called a signal peptide, which generally consists of 15 to 30 amino acids. This signal peptide, which has a decisive role in the secretion of the polypeptide, is cleaved during the process, thereby releasing the mature polypeptide in the periplasm.

The first studies concerned with adapting bacteria to the periplasmic production of a polypeptide which was foreign to them, and especially a polypeptide of eukaryotic origin, consisted in transforming the bacteria with the aid of an expression vector carrying a DNA sequence coding for a natural precursor of said polypeptide. This strategy has repeatedly proved to be rather unsuitable for industrial production in terms of quantity.

An attempt to provide a satisfactory solution consisted in replacing the natural signal peptide of the polypeptide with that of a bacterial polypeptide synthesized in the form of a precursor. European patent application A-0177343 gives Examples of how to use such signal peptides.

SUMMARY OF THE INVENTION

The applicant, observing that the choice of a bacterial signal peptide can determine the adoption, by the precursor of a heterologous polypeptide (especially of eukaryotic origin), of an inappropriate secondary conformation as said precursor is synthesized in the bacterium, has designed a novel signal peptide which affords a good yield for the periplasmic production of biologically active heterologous polypeptides.

The invention therefore relates to a novel signal peptide of the formula

MXKSTLLLLFLLLCLPSWNAGA in which

| | |
|---|---|
| A = Alanine | M = Methionine |
| C = Cysteine | N = Asparagine |
| F = Phenylalanine | P = Proline |
| G = Glycine | S = Serine |
| K = Lysine | T = Threonine |
| L = Leucine | W = Tryptophan | and X represents a direct bond between M and K, an amino acid selected from the group comprising the 20 amino acids of the genetic code, or a peptide containing 2, 3 or 4 amino acids selected, each independently of the other, from the group comprising the 20 amino acids of the genetic code.

DETAILED DESCRIPTION

A particularly valuable signal peptide is the one in which X represents a direct bond between M and K, or all or part of the peptide of the sequence APSG.

According to another aspect, the invention relates to the DNA sequences coding for the signal peptide according to the invention. Any sequences permitted by the degeneracy of the genetic code can be used. The following two sequences are particularly valuable:

5' ATG—GCT—CCA—TCT—GGC—AAA—TCC—ACG—CTG
CTT—CTC—TTA—TTT—CTG—CTC—CTG—TGC—CTG
CCC—TCT—TGG—AAC—GCC—GGC—GCT 3' which codes for the signal peptide of formula (1):

MAPSGKSTLLLLFLLLCLPSWNAGA and

5' ATG—AAA—TCC—ACG—CTG—CTT—CTC—TTA—TTT—CTG
CTC—CTG—TGC—CTG—CCC—TCT—TGG—AAC—GCC—GGC—
GCT—3' which codes for the signal peptide of formula (2):

MKSTLLLLFLLLCLPSWNAGA

The invention further relates to the expression vectors carrying a DNA sequence coding for a precursor of a polypeptide, wherein that portion of this sequence which codes for the signal peptide is a sequence according to the invention.

The signal peptide according to the invention, the DNA sequences coding for it and the expression vectors carrying these sequences can be applied to the periplasmic production of polypeptides by bacteria giving a negative response to Gram's staining test (so-called Gram-negative bacteria), transformed by these vectors.

The invention therefore further relates to the Gram-negative bacteria transformed by the vectors defined above. Among these bacteria, those belonging to the species *Escherichia coli* are of value. Preferably, the latter carry one or more mutations (stable if possible), for example mutations by deletion, affecting the cya gene and/or the crp gene.

According to another aspect, the invention relates to a process for the periplasmic production of a polypeptide, which consists in cultivating the cells of Gram-negative bacteria defined above, in subjecting the cells to an osmotic shock and in separating the recombinant polypeptide from the osmotic shock supernatant.

The process according to the invention is suitable for a production according to an inducible mode, where the expression of the DNA sequence coding for the precursor is placed under the control of an inducible promoter, as well as a production according to a constitutive mode, where the production of the polypeptide is continuous as soon as culture of the transformed strain has started.

The process according to the invention is suitable for the production of all kinds of polypeptides which are heterologous relative to the strain used. Thus it is appropriate for the production of polypeptides of eukaryotic origin. These can be proteins in the strict sense, such as human growth hormone (hGH) in particular, or peptides of smaller size, such as, in particular, a natural form or a variant of hirudin, for example the variant $(Lys^{47})$ HV2.

BRIEF DESCRIPTION OF THE DRAWINGS

The present invention will now be described in greater detail with the aid of three Examples in which reference will be made to the five Figures attached.

 = Location of the origin of replication (ORI).

 = DNA segment derived from plasmid pBR322.

 = DNA segment containing the sequence coding for a natural precursor of hGH.

 = DNA segment of phage fd containing a transcription terminator.

 = DNA segment containing a UV5 tryptophan-lactose hybrid promoter-operator.

 = DNA segment coding for β-lactamase (ApR): ampicillin resistance).

Figure 2:
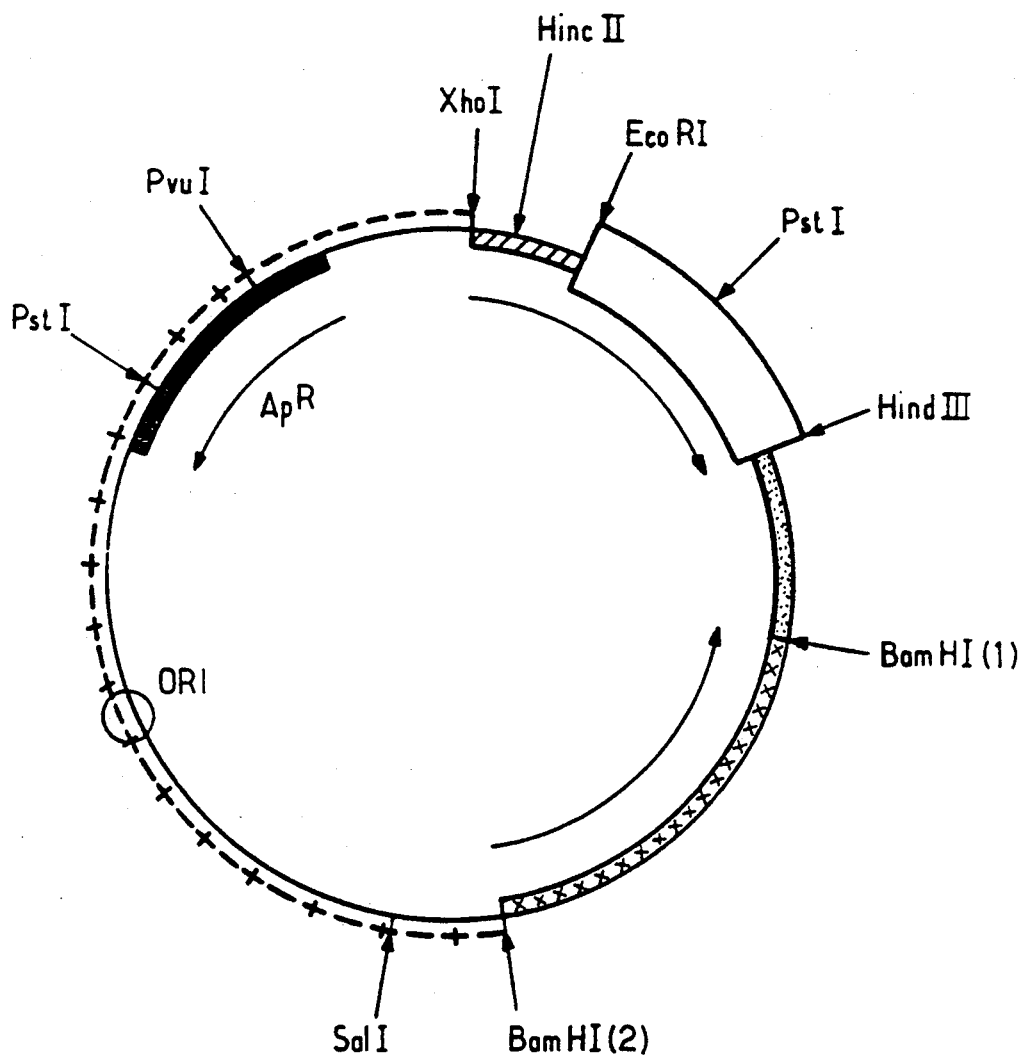

FIG. 2 shows the restriction map of plasmid p160,1, whose PvuI-XhoI-BamHI(1) and PvuI-ORI-BamHI(2) fragments originate from plasmids p163,1 and pBR327 respectively and whose small BamHI(2)-BamHI(1) fragment is fragment 3 described in Example 1 below.

Figure 3:
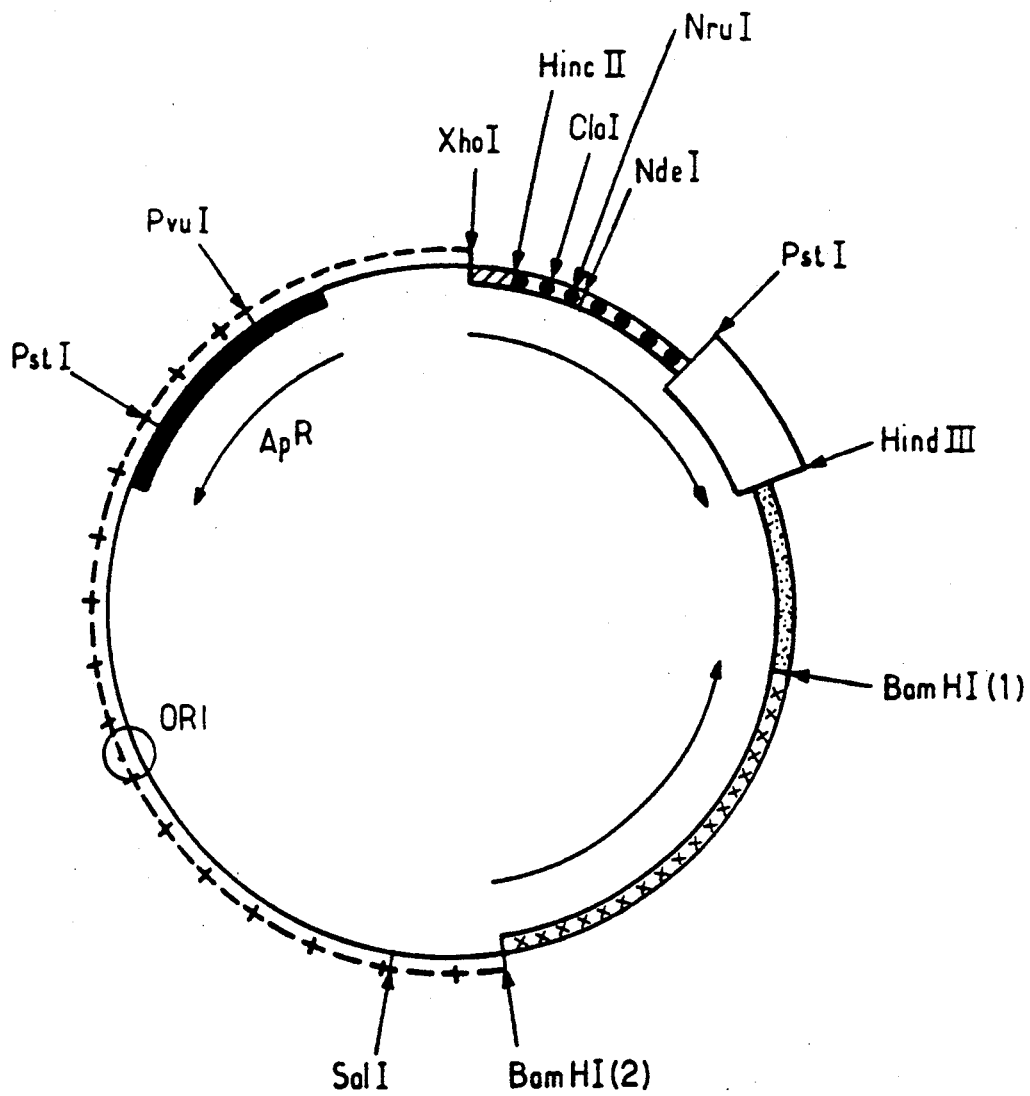

FIG. 3 shows a restriction map common to plasmids p380,1 and p373,2. The different restriction segments are labeled arbitrarily according to the following legend:

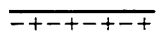 = PvuI-BamHI(2) sequence derived from plasmid pBR327.

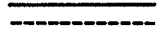 = PvuI-XhoI sequence derived from plasmid p163,1.

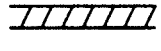 = XhoI-HincII sequence derived from plasmid p163,1.

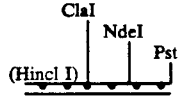 = Fragment 4 described in Example 1 below.

 = Fragment 3 described in Example 1 below.

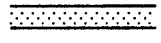 = DNA segment of phage fd containing a transcription terminator.

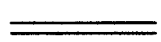 = PstI-HindIII fragment of the DNA segment containing the sequence coding for the natural precursor of hGH.

Figure 4:
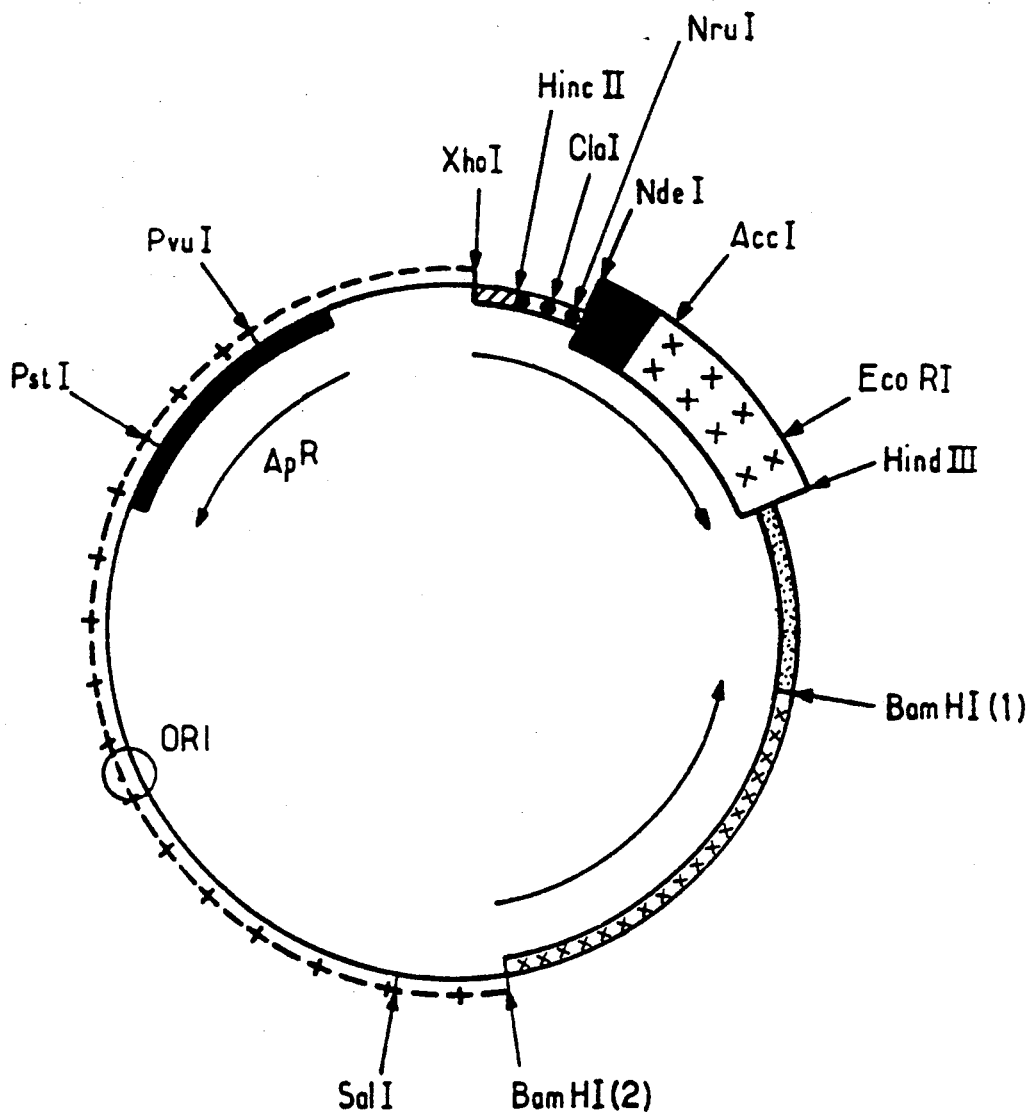

FIG. 4 shows the restriction map of plasmid p400,18. The different restriction fragments are defined arbitrarily according to the following legend:

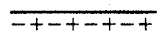 = PvuI-BamHI(2) sequence derived from plasmid pBR327.

 = PvuI-XhoI sequence derived from plasmid p163,1.

 = XhoI-HincII sequence derived from plasmid p163,1.

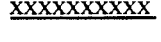 = Fragment 3 described in Example 1 below.

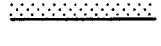 = DNA segment of phage fd containing a transcription terminator.

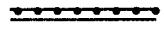 = DNA segment comprising in particular the promoter of the precursor of hirudin (HincII-NdeI part of fragment 4).

 = Coding sequence of the precursor of hirudin, comprising the sequence coding for the signal peptide of formula (1), represented by the black part of this symbol (combination of fragments 5 and 7).

Figure 5:
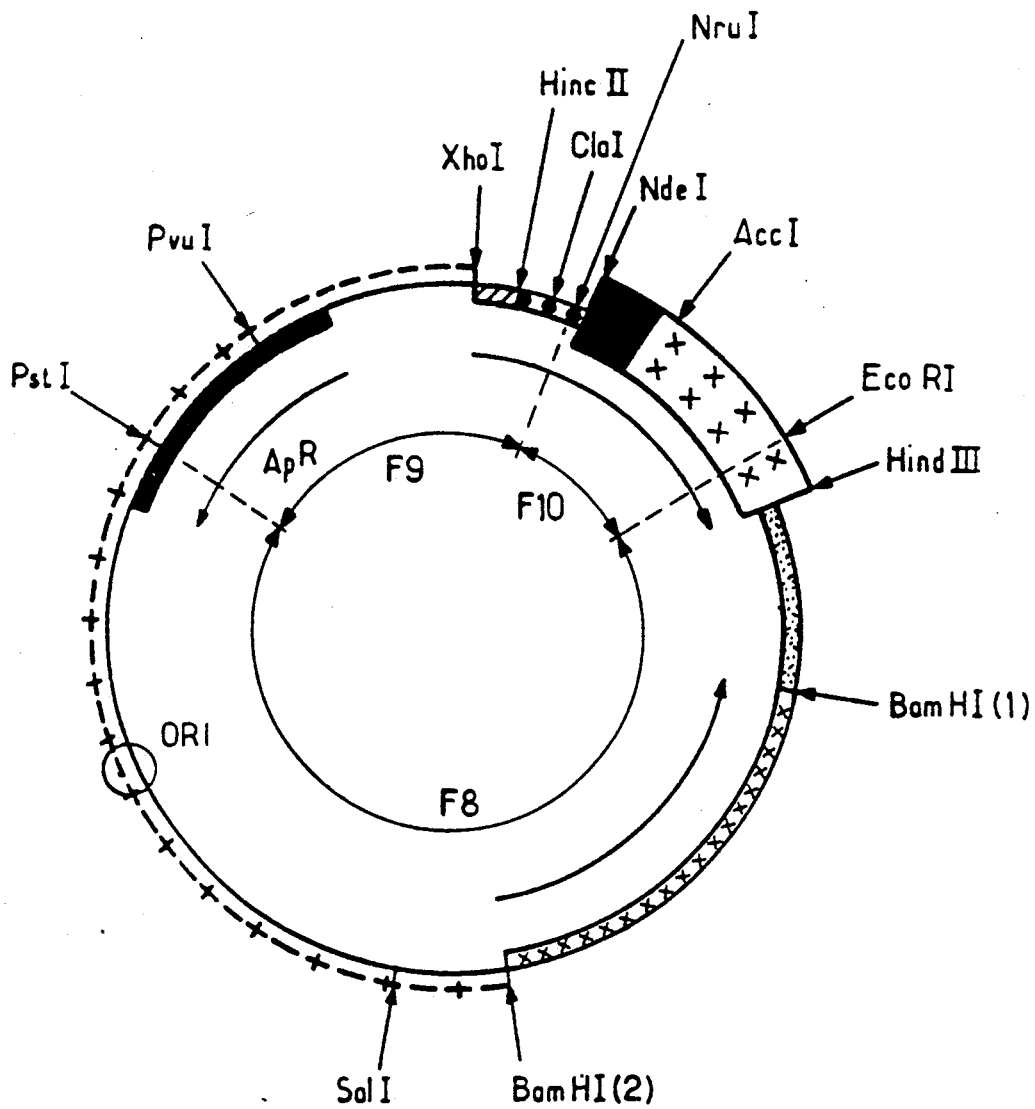

FIG. 5 shows the restriction map of plasmid p460. The different fragments are defined arbitrarily according to the following legend:

−+−+−+−+ = PvuI-BamHI(2) sequence derived from plasmid pBR327.

———————— = PvuI-XhoI sequence derived from plasmid p163,1.

///////// = XhoI-HincII sequence derived from plasmid p163,1.

XXXXXXXXXX = Fragment 3 described in Example 1 below.

::::::::::::: = DNA segment of phage fd containing a transcription terminator.

•••••••• = DNA segment comprising in particular the promoter of the precursor of hirudin (HincII-NdeI part of fragment 4).

▊XXXX
▊XXXX = Coding sequence of the precursor of hirudin, comprising the sequence coding for the signal peptide of formula (2), represented by the black part of this symbol.

EXAMPLE 1

Periplasmic Production of Human Growth Hormone with the Signal Peptide of the Formula MAPSGKSTLLLLFLLLCLPSWNAGA (1)

The strain used is a strain of the species *Escherichia moli* which is directly related to the strain described in European patent application A-0245138, deposited in the Collection Nationale de Cultures de Microorganismes (CNCM, Paris, France) on 17 February 1986 under the reference I-529. This strain carries a cya mutation by deletion and a crp mutation by deletion.

A plasmed carrying a DNA sequence coding for a precursor of hGH, whose signal peptide is the one according to the invention of formula (1)— MAPSGKSTLLLLFLLLCLPSWNAGA—was prepared. This plasmid was called p398.

1. Construction of plasmed p398

1a) Construction of plasmid p373,2

The strategy employed utilizes fragments obtained from already existing plasmids available to the public and fragments prepared by synthesis according to the techniques now in common use. The cloning techniques employed are those described by T. MANIATIS, E. F. FRITSCH and J. SAMBROOK in "Molecular cloning, a laboratory manual" (Cold Spring Harbor Laboratory, 1984). The oligonucleotides are synthesized using a Biosearch 4600 DNA synthesizer.

Figure 1:
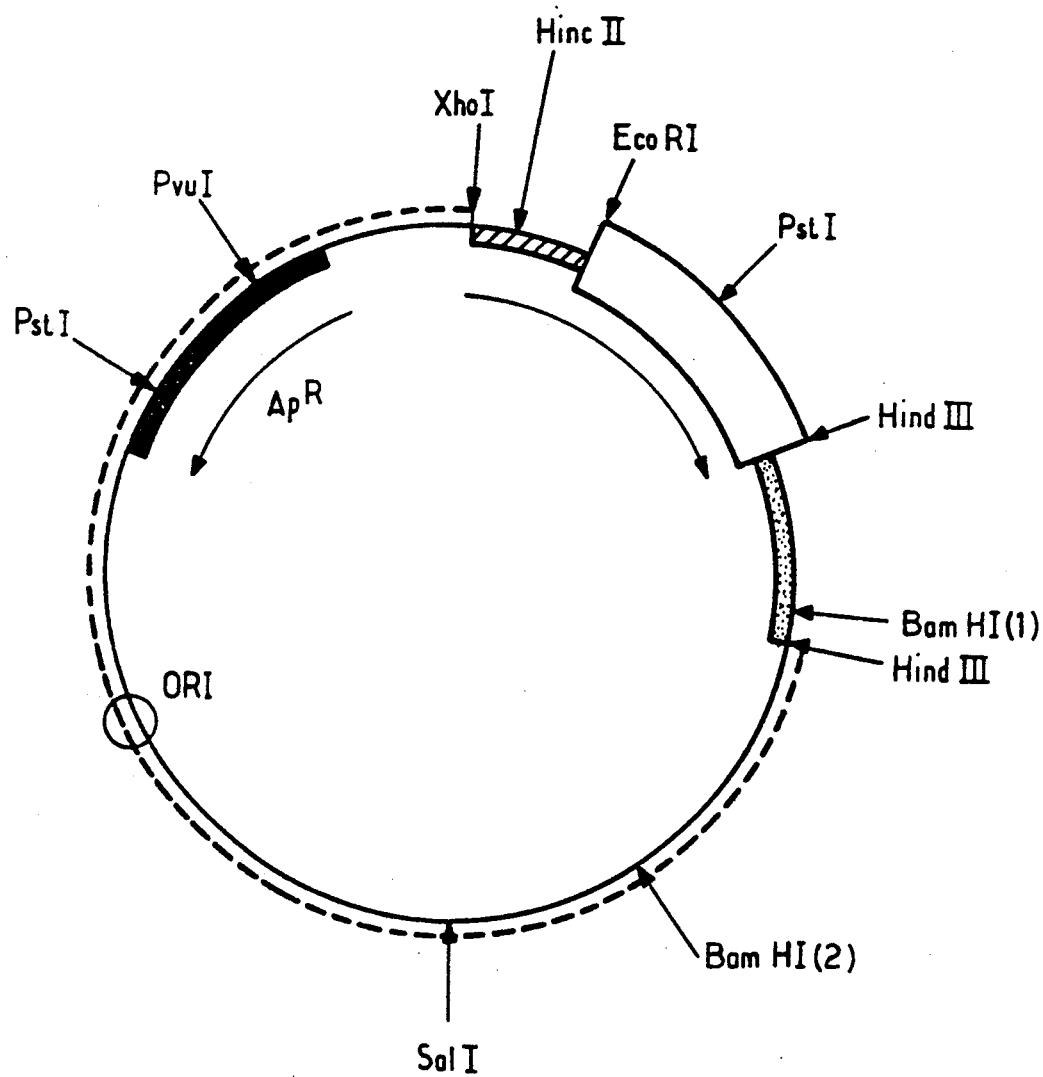
FIG. 1 shows a restriction map of plasmid p163,1. The different restriction segments are labeled arbitrarily according to the following legend.

Plasmid P163,1 (FIG. 1), described in European patent application A-0245138 (shown in FIG. 2 of this document, which does not mark the BamHI(l) site shown in FIG. 1 of the present patent application) and present in the strain deposited in the CNCM under the reference I-530 on 17 February 1986, was digested with the enzymes PvuI and BamHI. This plasmid contains the gene coding for hGH. The PvuI-BamHI(l,) fragment—hereafter fragment 1—containing the action site of the restriction enzyme XhoI, shown in FIG. 1, was purified.

Likewise, plasmid pBR327, well known to those skilled in the art (q.v. SOBERON, X. et al., Gene, 9 (1980) 287-305), was digested with the enzymes PvuI and BamHI. The PvuI-BamHI(2) fragment—hereafter fragment 2—containing the origin of replication, was purified.

Fragment 3 was then prepared; this is a synthetic BamHI(1)-BamHI(2) fragment containing the lac i gene and its promoter and having the following DNA sequence, on which the two ends of the strand are identified by the numbers 1 and 2 in order to specify the orientation of the fragment in the plasmids described in FIGS. 2 and 3:

| FRAGMENT 3 | | | | |
|---|---|---|---|---|
| BamHI(1) | | | | |
| GATCC | GCGGAAGCAT | AAAGTGTAAA | GCCTGGGGTG | CCTAATGAGT |
| GAGCTAACTT | ACATTAATTG | CGTTGCGCTC | ACTGCCCGCT | TTCCAGTCGG |
| GAAACCTGTC | GTGCCAGCTG | CATTAATGAA | TCGGCCAACG | CGCGGGGAGA |
| GGCGGTTTGC | GTATTGGGCG | CCAGGGTGGT | TTTTCTTTTC | ACCAGTGAGA |
| CGGGCAACAG | CTGATTGCCC | TTCACCGCCT | GGCCCTGAGA | GAGTTGCAGC |
| AAGCGGTCCA | CGCTGGTTTG | CCCCACCACC | CGAAAATCCT | GTTTGATGGT |
| GGTTAACGGC | GGGATATAAC | ATGAGCTGTC | TTCGGTATCG | TCGTATCCCA |
| CTACCGAGAT | ATCCGCACCA | ACGCGCAGCC | CGGACTCGGT | AATGGCGCGC |
| ATTGCGCCCA | GCGCCATCTG | ATCGTTGGCA | ACCAGCATCG | CAGTGGGAAC |
| GATGCCCTCA | TTCAGCATTT | GCATGGTTTG | TTGAAAACCG | GACATGGCAC |
| TCCAGTCGCC | TTCCCGTTCC | GCTATCGGCT | GAATTTGATT | GCGAGTGAGA |
| TATTTATGCC | AGCCAGCCAG | ACGCAGACGC | GCCGAGACAG | AACTTAATGG |
| GCCCGCTAAC | AGCGCGATTT | GCTGGTGACC | CAATGCGACC | AGATGCTCCA |
| CGCCCAGTCG | CGTACCGTCT | TCATGGGAGA | AAATAATACT | GTTGATGGGT |
| GTCTGGTCAG | AGACATCAAG | AAATAACGCC | GGAACATTAG | TGCAGGCAGC |
| TTCCACAGCA | ATGGCATCCT | GGTCATCCAG | CGGATAGTTA | ATGATCAGCC |
| CACTGACGCG | TTGCGCGAGA | AGATTGTGCA | CCGCCGCTTT | ACAGGCTTCG |
| ACGCCGCTTC | GTTCTACCAT | CGACACCACC | ACGCTGGCAC | CCAGTTGATC |
| GGCGCGAGAT | TTAATCGCCG | CGACAATTTG | CGACGGCGCG | TGCAGGGCCA |
| GACTGGAGGT | GGCAACGCCA | ATCAGCAACG | ACTGTTTGCC | CGCCAGTTGT |
| TGTGCCACGC | GGTTGGGAAT | GTAATTCAGC | TCCGCCATCG | CCGCTTCCAC |
| TTTTTCCCGC | GTTTTCGCAG | AAACGTGGCT | GGCCTGGTTC | ACCACGCGGG |
| AAACGGTCTG | ATAACAGACA | CCGGCATACT | CTGCGACATC | GTATAACGTT |
| ACTGGTTTCA | CATTCACCAC | CCTGAATTGA | CTCTCTTCCG | GGCGCTATCA |
| TGCCATACCG | CGAAAGGTTT | TGCGCCATTC | GATGGTGTCC | G          3' |
| | | | | BamHI(2) |

Fragments 1, 2 and 3 were then ligated to give plasmid p160, 1 shown in FIG. 2.

This plasmid was subjected to partial digestion with the restriction enzymes HincII and PstI. The large HincII-PstI fragment, containing the origin of replication and shown in FIG. 2, was then ligated to fragment 4 shown below, which is a synthetic DNA fragment carrying a sequence coding for the first 44 amino acids of a natural precursor of hGH and, upstream from this sequence, regulatory signals.

1b) Construction of plasmid p398

Finally, plasmid p373,2 was digested with the restriction enzymes NdeI and XbaI so as to remove the NdeI-XbaI fragment of fragment 4 above and replace it with the synthetic NdeI-XbaI fragment shown below:

FRAGMENT 4

```
                    ClaI
5' TCGAGCTGACTGACCTGTTGCTTATATTACATCGA
   AGCTCGACTGACTGGACAACGAATATAATGTAGCT

NdeI
   TACGCTATAATGTGTGGAATTGTGAGCGATAACAATTTCACACAGTTTAACTTTAAGAAGGAGATATACAT
   ATGCGATATTACACACCTTAACACTCGCCTATTGTTAAAGTGTGTCAAATTGAAATTCTTCCTCTATATGTA

ATG GCT ACC GGA TCC CGG ACT AGT CTG CTC CTG GCT TTT GGC CTG CTC TGC CTG
   TAC CGA TGG CCT AGG GCC TGA TCA GAC GAG GAC CGA AAA CCG GAC GAC ACG GAC
    M   A   T   G   S   R   T   S   L   L   L   A   F   G   L   L   C   L
   -26

XbaI
   CCC TGG CTT CAA GAG GGC AGT GCC TTC CCA ACC ATT CCC TTA TCT AGA CTT TTT
   GGG ACC GAA GTT CTC CCG TCA CGG AAG GGT TGG TAA GGG AAT AGA TCT GAA AAA
    P   W   L   Q   E   G   S   A   F   P   T   I   P   L   S   R   L   F

GAC AAC GCT ATG CTC CGC GCC CAT CGT CTG CAC CAG CTG GCC TTT GAC ACC TAC
   CTG TTG CGA TAC GAG GCG CGG GTA GCA GAC GTG GTC GAC CGG AAA CTG TGG ATC
    D   N   A   M   L   R   A   H   R   L   H   Q   L   A   F   L   T   Y

PstI
   CAG GAG TTT GAA GAA GCC TAT ATC CCA AAG GAA CAG AAG TAT TCA TTC CTG CA
   GTC CTC AAA CTT CTT CGG ATA TAG GGT TTC CTT GTC TTC ATA AGT AAG G      5'
    Q   E   F   E   E   A   Y   I   P   K   E   Q   K   Y   S   F
                                                                44
```

In this fragment, the amino acids are designated by letters according to the following code:

| | |
|---|---|
| A = Alanine | M = Methionine |
| C = Cysteine | N = Asparagine |
| D = Aspartic acid | P = Proline |
| E = Glutamic acid | Q = Glutamine |
| F = Phenylalanine | R = Arginine |
| G = Glycine | S = Serine |
| H = Histidine | T = Threonine |
| I = Isoleucine | V = Valine |
| K = Lysine | W = Tryptophan |
| L = Leucine | Y = Tyrosine |

Sequences −35 (TTGCTT) and −10 (TATAAT) of the promoter sequence, and the Shine-Dalgarno sequence well known to those skilled in the art, are underlined in that order in this fragment.

Plasmid p380,1 was obtained in this way.

Plasmid p380,1 (FIG. 3) was then digested with the restriction enzymes ClaI and NdeI so as to remove the small ClaI-NdeI fragment of fragment 4 above and replace it with the ClaI-NdeI fragment below:

```
   ClaI
5' CGATAGCGTATAATGTGTGGAATTGTGAGCGGATAACA
      TATCGCATATTACACACCTTAACACTCGCCTATTGT

NruI
           ▼                          NdeI
   ATTTCACACAGTTTTTCGCGAAGAAGGAGATATACA
   TAAAGTGTGTCAAAAAGCGCTTCTTCCTCTATATGTAT  5'
                   ▲
```

The resulting plasmid is plasmid p373,2 (FIG. 3).

```
              NdeI
              ┌─▶
5' TATG GCT CCA TCT GGC AAA TCC ACG CTG
       AC CGA GGT AGA CCG TTT AGG TGC GAC
   CTT CTC TTA TTT CTG CTC CTG TGC CTG
   GAA GAG AAT AAA GAC GAG GAC ACG GAC

⬇
   CCC TCT TGG AAC GCC GGC GCT TTC CCA
   GGG AGA ACC TTG CGG CCG CGA AAG GGT

XbaI
   ACC ATT CCC TTA T
   TGG TAA GGG AAT AGATC  5'
```

Plasmid p398 obtained in this way contains a particularly valuable DNA sequence coding for the signal peptide of formula (1). This sequence is delimited above by two arrows.

2. General methodology

The experiments were performed on 6 clones of plasmid p398 (clones 2, 3, 5, 6, 7 and 8), the results being assessed relative to plasmid p373,2, which contains a DNA sequence coding for the natural precursor of hGH. The experiments consisted in cultivating the host-vector systems in question, prepared beforehand (cf. $\eta$ 2.1), under conditions such as to give an adequate biomass (cf. $\eta$ 2.2) and such that the cells subjected to induction produce hGH (cf. $\eta$ 2.3), in collecting the proteins contained in the periplasmic space by osmotic shock (cf. $\eta$ 2.4), in subjecting the bacteria to total lysis to give a total protein extract (cf. $\eta$ 2.5), in determining the periplasmic hGH collected in 2.4 (cf. $\eta$ 2.6) and in analyzing the supernatants obtained in 2.4 and in 2.5 by the Western Blot technique (cf. $\eta$ 2.7).

2.1 Preparation of the host-vector systems

The host-vector systems were prepared according to the bacterial transformation techniques known to those skilled in the art, which are described especially in the following books:
Molecular cloning—A Laboratory Manual—T. Maniatis, E. F. Fritsch and J. Sambrook—Cold Spring Harbor Laboratory—1982.
Experiments in Molecular Genetics—J. H. MILLER—Cold Spring Harbor Laboratory—1972.

2.2 Culture a) Inoculation

An isolated colony obtained on a solid medium (LB medium+agar-agar) was suspended in 5 ml of a medium (LB medium).

The LB medium used has the following characteristics:
its components introduced before autoclaving are:

| Bactotryptone | 10 g |
|---|---|
| yeast extract | 5 g |
| sodium chloride | 5 g |
| distilled water | qs 1 l | its pH is adjusted to 7.3 before autoclaving;
ampicillin is added after autoclaving at a rate of 100 $\mu$g/ml.

b) Incubation

The suspension prepared in a) was incubated at 37° C. for 18 h in order to allow the culture to reach the stationary growth phase. The dense suspension obtained was diluted in LB medium to give an optical density value close to 0.03 when read at 600 nm—OD at 600 nm—and 25 ml of this bacterial suspension were then incubated at 37° C., with agitation, until the OD at 600 nm was of the order of 0.3.

2.3 Induction

Isopropyl-$\beta$-D-thiogalactose (or IPTG) was added to the bacterial suspension obtained according to 2.2.b in an amount such that, its final concentration was equal to 1 mM; IPTG was used here to initiate and maintain the synthesis of the precursor of hGH by neutralizing the action of the repressor which normally binds to the lactose operator.

The suspension, with IPTG added, was agitated at 37° C. for 2 h 30 min.

2.4 Osmotic shock

Reference was made to the protocol described by N. G. NOSSAL and L. A. HEPPEL in "The Journal of Biological Chemistry, 241 (1966) 3055-3063".

a) Washing with Tris and EDTA

A sample of the suspension as obtained in 2.3 after induction was taken and centrifuged for 5 minutes at 6000 g.

The residue was taken up in a volume of buffer at PH 7 (solution A) (cf. above) such that the suspension obtained had an OD at 600 nm of the order of 10.

The buffer used was prepared by adding the following to distilled water:
tri(hydroxymethyl)aminomethane-HCl, or Tris-HCl, added so as to give a final concentration of 30 mM.
ethylenediaminetetraacetic acid, or EDTA, added so as to give a final concentration of 1 mM.

b) Action of sucrose

The suspension obtained in 2.4.a was centrifuged for 5 minutes at 6000 g.

The residue was taken up very carefully, at constant volume, in a solution B prepared for immediate use and corresponding to solution A to which sucrose has been added at a rate of 15 g per 100 ml.

The suspension was left for 10 minutes at 20° C. It was then centrifuged for 5 minutes at 6000 g. The centrifuge tubes were placed in melting ice.

The supernatant was carefully removed and replaced (at constant volume) with deionized water which had been cooled beforehand to the temperature of melting ice.

The suspension prepared in this way (having an OD at 600 nm of the order of 10) was left for 5 minutes at 0° C.

c) Collection of the proteins located in the periplasm

The suspension obtained in 2.4.b was centrifuged for 10 minutes at 18,000 g.

The supernatant, which contained the proteins located in the periplasm, was collected.

2.5 Total lysis

A sample of the suspension as obtained in 2.3 after induction was taken and centrifuged in an Eppendorf tube for 5 minutes at 6000 g.

The residue was resuspended in a volume of buffer such that 1 ml of suspension had an OD at 600 nm of 0.2.

The buffer was prepared from a twice concentrated buffer comprising a solution of the following in distilled water:
Tris-HCl 0.125 M, pH 6.8;
sodium dodecylsulfate (4% (w/v));
glycerol (20% (w/v));
$\beta$-mercaptoethanol (10% (w/v));
bromophenol blue (0.02% (v/v)).

The tube was placed for 10 minutes in a water bath set at 100° C., the suspension was then centrifuged for 5 minutes at 6000 g and the supernatant was collected.

2.6 Determination of the periplasmic hGH

The supernatant obtained in 2.4.c was subjected to high pressure liquid chromatography using an apparatus equipped with a calibrated injection system and a detector set at 220 nm.
The following were used:
a C8 - 300 Angstrom reversed-phase column made of steel, with a length of 10 cm and an internal diameter of 4.6 mm (SYNCHROM reference C8 R103-10),
a mobile phase consisting of a linear gradient passing from 70 volumes of solution S1 and 30 volumes of solution S2 to 40 volumes of solution S1 and 60 volumes of solution S2 in 20 minutes.

Solutions S1 and S2 had the following characteristics:
S1 = purified water containing 0.1% (v/v) of trifluoroacetic acid,
S2 = acetonitrile for HPLC, containing 0.08% (v/v) of trifluoroacetic acid.

The flow rate was 1 ml per minute.

The optical density of the fractions was measured and the amount of periplasmic hGH, expressed in micrograms per ml of supernatant, was determined by comparison with a previously established standard scale.

2.7 Analysis by the Western Blot technique

The following operations were carried out in succession:
separation by gel electrophoresis (according to the protocol described by LAEMMLI, U. K., Nature, 227 (1970) 680–685) of the different proteins contained in each of the supernatants obtained according to 2.4.c and 2.5; the gel used was a polyacrylamide gel (15% w/v) containing 0.5% of sodium dodecylsulfate;
transfer of said proteins contained in the gel on to a nitrocellulose filter (according to the technique of H. TOWBIN et al., Proc. Natl. Acad. Sci. USA, 76 (1979) 4350–4354);
immunodetection performed according to the technique of BURNETTE (W. W. BURNETTE, Anal. Biochem., 112 (1981) 195–203); this entails the following successive operations:
rinsing the nitrocellulose filter for 10 minutes with a buffer A (Tris-HCl 10 mM, NaCl 170 mM, KI 1 mM);
bringing the nitrocellulose filter into contact with a buffer B (buffer A with bovine serum albumin added at a rate of 3 g per 100 ml) for 30 minutes at 37° C.;
bringing the nitrocellulose filter into contact with an immune serum (a polyclonal antibody recognizing mature hGH and its precursor) for 18 h at 20° C.;
rinsing the nitrocellulose filter with buffer B;
bringing the nitrocellulose filter into contact with a solution of protein A labeled with iodine 125 at a rate of 0.1 microcurie per ml, for 6 h at 20° C.;
rinsing the filter with buffer A;
drying the filter between two absorbent sheets;
bringing the filter into contact with an X-ray film;
developing the film.

3. Results

3.1 Determination of the periplasmic hGH

The results are reported in the Table below:

| | PLASMID TESTED | | | | | | |
|---|---|---|---|---|---|---|---|
| | Control | PLASMID 398 | | | | | |
| | 373,2 | 398,2 | 398,3 | 398,5 | 398,6 | 398,7 | 398,8 |
| Periplasmic hGH expressed in micrograms per ml of supernatant collected after osmotic shock and brought to a turbidity such that OD at 600 nm = 1 | 1.5 | 2.5 | 2.9 | 2.8 | 3.1 | 3.1 | 3.4 |

It is clearly apparent that plasmid 398 affords a periplasmic production which is about twice that afforded by plasmid 373,2.

3.2 Analysis by the Western Blot technique

Analysis of the autoradiographic films reveals that the precursor has not been detected in the extracts obtained after total lysis of the bacteria transformed with plasmid p398, whereas it is detected in the extracts obtained after total lysis of the bacteria transformed with clone p373,2. This shows that the signal peptide according to the invention is capable of permitting, with a high efficacy, the passage of the precursor through the cytoplasmic membrane and its concomitant maturation.

These results emphasize the great advantage of using the signal peptide according to the invention of formula (1) for the periplasmic production of a protein such as human growth hormone.

EXAMPLE 2

Periplasmic Production of a Hirudin Variant with the Signal Peptide of the Formula
MAPSGKSTLLLLFLLLCLPSWNAGA (1)

1. Strain and plasmid

The strain described in Example 1 was used.

A plasmid called p400 was constructed from plasmid p373,2. It carries a DNA sequence coding for the variant (Lys$^{47}$) HV2 described in European patent application A-0273800, the formula of which is reproduced below:

| Ile | Thr | Tyr | Thr | Asp | Cys | Thr | Glu | Ser | Gly | Gln | Asn | Leu | Cys | Leu |
|---|---|---|---|---|---|---|---|---|---|---|---|---|---|---|
| Cys | Glu | Gly | Ser | Asn | Val | Cys | Gly | Lys | Gly | Asn | Lys | Cys | Ile | Leu |
| Gly | Ser | Asn | Gly | Lys | Gly | Asn | Gln | Cys | Val | Thr | Gly | Glu | Gly | Thr |
| Pro | Lys | Pro | Glu | Ser | His | Asn | Asn | Gly | Asp | Phe | Glu | Glu | Ile | Pro |
| Glu | Glu | Tyr | Leu | Gln | | | | | | | | | | | said DNA sequence being preceded by a sequence coding for the signal peptide according to the invention of formula (1).

Construction of plasmid p400

A synthetic AccI-HindIII fragment (fragment 5) containing a sequence coding for this variant (except the first 3 amino acids) was prepared. It is shown below, the codon corresponding to the last amino acid being designated by an arrow:

FRAGMENT 5

AccI
5' AT ACA GAC TGC ACA GAA TCG GGT
TGT CTG ACG TGT CTT AGC CCA

-continued
FRAGMENT 5

CAA ATT TTG TGC CTC TGC GAG GGA AGC AAT
GTT TTA AAC ACG GAG ACG CTC CCT TCG TTA

GTT TGC GGT AAA GGC AAT AAG TGC ATA TTG
CAA ACG CCA TTT CCG TTA TTC ACG TAT AAC

GGT TCT AAT GGA AAG GGC AAC CAA TGT GTC
CCA AGA TTA CCT TTC CCG TTG GTT ACA CAG

ACT GGC GAA GGT ACA CCG AAA CCT GAA AGC
TGA CCG CTT CCA TGT GGC TTT GGA CTT TCG

CAT AAT AAC GGC GAT TTC GAA GAA ATT CCA
GTA TTA TTG CCG CTA AAG CTT CTT TAA GGT

↓

GAA GAA TAT TTA CAA TGA AAA ATG AAA GAA
CTT CTT ATA AAT GTT ACT TTT TAC TTT CTT

Eco RI
▼
TAT CAA TCA TAG AGA ATT TTG ATT TGG GAA
ATA GTT AGT ATC TCT TAA AAC TAA ACC CTT

TTC GAA AAG TTC GCT GGT ACT AAG GCT TTG
AAG CTT TTC AAG CGA CCA TGA TTC CGA AAC
▲

TTA GAC GAA GTT GTC AAG AGC TCT GCT GCT
AAT CTG CTT CAA CAG TTC TCG AGA CGA CGA

GGT AAC ACC GTC ATC ATT GGT GGT GGT GAC
CCA TTG TGG CAG TAG TAA CCA CCA CCA CTG

ACT GCC ACT GTC GCT AAG AAG TAC GGT GTC
TGA CGG TGA CAG CGA TTC TTC ATG CCA CAG

HindIII
ACT GAC AAG ATC CCA
TGA CTG TTC TAG GGT TCG A - 5'

Plasmid p373,2 was digested with the restriction enzymes NdeI and HindIII and the NdeI-HindIII fragment (fragment 6), containing the origin of replication, as shown in FIG. 3, was purified.

A synthetic NdeI-AccI fragment (fragment 7) was prepared; its sequence is given below:

FRAGMENT 7

NdeI
⟶

5' TATGGCTCCATCTGGCAAATCCACGCTGCTTCTCTTATTTCTGCTCCTGTGCCTGCCCTCT—
ACCGAGGTAGACCGTTTAGGTGCGACGAAGAGAATAAAGACGAGGACACGGACGGGAGA—

AccI
↓

TGGAACGCCGGCGCTATTACGT
ACCTTGCGGCCGCGATAATGCATA 5'

This fragment contains a particularly valuable DNA sequence coding for the signal peptide of formula (1), which sequence has been delimited by two arrows and is followed by nucleotides corresponding to the first 3 codons of the hirudin variant (LyS$^{47}$) HV2.

Fragments 5, 6 and 7 were ligated; the plasmid obtained is plasmid p400, which is shown in FIG. 4.

2. General methodology

Plasmid p400 was introduced by transformation into the bacterial strain described in Example 1.

The experiments were performed in parallel on two different clones (clones p400,18 and p400,24) in accordance with the procedure described in sections 2.1 and 2.2 of Example 1. The cultures were induced by the method indicated in section 2.3 of Example 1, with two modifications: induction was initiated by adding IPTG when the culture had reached an OD at 600 nm of about 0.5, and it was maintained for 3 h 30 min in a first experiment and for 17 h in a second experiment.

After induction, the cells were subjected to an osmotic shock (cf. η 2.4, Example 1) and the antithrombin activity of the hirudin in the supernatant collected was measured.

This activity was determined using the technique described by Markwardt, F. et al. (Thromb. Haemostas., 52 (19) 160-163) and discussed in detail by Harvey, R. P. et al. (Proc. Natl. Acad. Sci. USA, 83 (1986) 1084-1088).

The hirudin variant obtained from one of the clones was purified by high pressure liquid chromatography and its NH$_2$-terminal sequence was determined.

3. Results

The results are reported in the Table below.

They are expressed in antithrombin units per ml of supernatant collected after osmotic shock and brought to a turbidity such that OD at 600 nm = 10.

|  |  | Plasmid p400 | |
|---|---|---|---|
|  |  | clone p400,18 | clone p400,24 |
| Induction time | 3 h 30 min | 241 | 369 |
|  | 17 h | 1595 | 983 |

As the known values of the specific antithrombin activity of hirudin are between 13,000 and 17,700 antithrombin units per mg of hirudin (Loison, G. et al., Bio/Technology, 6:72-77 (1988)), it can be deduced that, after 17 h of induction, from 5 to 10 mg of hirudin have been extracted per liter of supernatant of OD at 600 nm = 1.

Such an amount is much greater than that described by Dodt, J. et al., FEBS, 202 (1986) 373-377, with the hirudin variant HV1 produced in the periplasm in a strain of E. coli transformed with a plasmid carrying a sequence coding for a hybrid precursor of hirudin, the signal peptide of which is that of alkaline phosphatase.

It has furthermore been observed that the hirudin produced by clone p400,18 does indeed have the NH$_2$-terminal end characteristic of the variant (Lys$^{47}$) HV2.

These results show that the signal peptide according to the invention of formula (1) is appropriate for the efficient periplasmic production of a peptide such as the hirudin variant (Lys$^{47}$) HV2.

EXAMPLE 3

Periplasmic Production of a Hirudin Variant with the Signal Peptide of the Formula MKSTLLLLFLLLCLPSWNAGA

1. Strain and plasmid

The strain described in Example 1 was used.

The strategy employed to construct plasmid p460, comprising a sequence coding for the hirudin variant (Lys[47]) HV2 described in European patent application A-0273800, which sequence is preceded by a sequence coding for the signal peptide according to the invention of formula (2):

MKSTLLLLFLLLCLPSWNAGA utilizes DNA fragments obtained from plasmid p400,18 described in Example 2 and a fragment obtained after directed mutagenesis in phage M13mp19 marketed by Amersham.

Construction of plasmid p460

1a) Fragments obtained from plasmid p400,18

α) Plasmid p400,18 was digested with the enzymes PstI and EcoRI. The PstI-EcoRI fragment of 3868 bp containing the origin of replication, hereafter called fragment 8 (shown in FIG. 5 as F8), was purified.

β) Plasmid p400,18 was digested with the enzymes NruI and PstI. The small NruI-PstI fragment of 1062 bp containing the promoter, hereafter called fragment 9 (shown in FIG. 5 as F9), was purified.

1b) NruI-EcoRI fragment obtained from phage M13mp19

α) The XhoI-EcoRI fragment of 650 bp derived from plasmid 400,18 by digestion with the enzymes XhoI and EcoRI and purification, which contains the sequence coding for the signal peptide of formula (1), was inserted into the polylinker (cloning polysite) of phage M13mp19 (Amersham) at the restriction sites SalI/EcoRI. Ligation of the XhoI and SalI sites caused these two sites to disappear.

α) An oligonucleotide of 63 nucleotides having the following sequence:

```
5' - ATG—AAA—TCC—ACG—CTG—CTT—CTC—TTA—TTT—
    CTG—CTC—CTG—TGC—CTG—CCC—TCT—TGG—AAC—
    GCC—GGC—GCT - 3'
``` was synthesized. This sequence codes for the signal peptide of formula (2).

The technique of directed mutagenesis in vitro, performed with the aid of the Amersham 1523 kit, was used to construct a fragment which carried a mutation, as regards the sequence coding for the signal peptide, relative to the fragment obtained in α). This technique, which is described in detail in the booklet accompanying this kit, consists of the introduction of an XhoI-EcoRI fragment of 650 bp (cf. section α) above) into the double-stranded form of phage M13mp19, the purification of the single-stranded form of this recombinant phage, the hybridization of the above-mentioned oligonucleotide of 63 nucleotides and the action of the Klenow fragment of DNA polymerase and then T4 ligase to give a double-stranded circular form of the recombinant phage, one of the strands of which carries the desired mutation.

γ) The phage containing the mutated DNA fragment was digested with the enzymes NruI and EcoRI. The NruI-EcoRI fragment containing the sequence coding for the signal peptide of formula (2) and the sequence coding for the hirudin variant (Lys[47]) HV2, hereafter called fragment 10 (shown in FIG. 5 as F10), was purified.

Fragments 8, 9 and 10 were ligated; the plasmid obtained is plasmid p460, which is shown in FIG. 5.

2. General methodology

Plasmid p460 was introduced by transformation into the bacterial strain described in Example 1.

The experiments were performed in parallel on two different clones (clones p460,2 and p460,4), in which the presence of the above-mentioned sequence of 63 nucleotides was checked, and on control clone p400,18, in accordance with the procedure described in sections 2.1 and 2.2 of Example 1. The cultures were induced by the method indicated in section 2.3 of Example 1, with two modifications: induction was initiated by adding IPTG when the culture had reached an OD at 600 nm of about 0.5, and it was maintained for 2 hours.

After induction, the cells were subjected to an osmotic shock (cf. section 2.4, Example 1) and the hirudin variant (Lys[47]) HV2 thereby released into the culture supernatant was determined by HPLC.

Determination of the hirudin variant (Lys[47]) HV2

The supernatant obtained after osmotic shock was subjected to high pressure liquid chromatography, HPLC, using an apparatus equipped with a calibrated injection system and a detector set at 220 nm.

The following were used:

a C8 - 300 Å reversed-phase column made of steel, with a length of 7.5 cm and an internal diameter of 4.6 mm (BECKMAN Ultrapore reference 238 771).

a mobile phase consisting of a linear gradient passing from 85 volumes of solution S1 and 15 volumes of solution S2 to 50 volumes of solution S1 and 50 volumes of solution S2 in 10 minutes.

Solutions S1 and S2 had the following characteristics:

S1 = purified water containing 0.1% (v/v) of trifluoroacetic acid.

S2 = acetonitrile for HPLC, containing 0.08% (v/v) of trifluoroacetic acid.

The flow rate was 2 ml per minute.

The optical density of the fractions was measured and the amount of periplasmic variant (Lys[47]) HV2, expressed in milligrains per liter of supernatant, was determined by comparison with a standard solution of variant (Lys[47]) HV2.

Results

The results are reported in the Tables below. They are expressed in mg/l of supernatant collected after osmotic shock and brought to an optical density at 600 nm of 1.

| | PLASMID TESTED | |
|---|---|---|
| 1st experiment | Control 400,18 | 460,2 |
| Hirudin variant (Lys⁴⁷) HV2 in mg/l of supernatant collected after osmotic shock and brought to OD at 600 nm = 1 | 1.3 | 3.1 |

| | PLASMID TESTED | | |
|---|---|---|---|
| 2nd experiment | Control 400,18 | 460,2 | 460,4 |
| Hirudin variant (Lys⁴⁷) HV2 in mg/l of supernatant collected after osmotic shock and brought to OD at 600 nm = 1 | 1.3 | 5.2 | 4.5 |

It is clear from the above Tables that the periplasmic production of the hirudin variant (Lys$^{47}$) HV2 afforded by plasmids 460,2 and 460,4 is considerably greater than that afforded by plasmid 400,18.

These results show that the signal peptide according to the invention of formula (2) is particularly appropriate for the efficient periplasmic production of a peptide such as the hirudin variant (Lys$^{47}$) HV2.

What is claimed is:

1. A DNA sequence coding for a signal peptide of the formula

MXKSTLLLLFLLLCLPSWNAGA in which:

| A = Alanine | M = Methionine |
|---|---|
| C = Cysteine | N = Asparagine |
| F = Phenylalanine | P = Proline |
| G = Glycine | S = Serine |
| K = Lysine | T = Threonine |
| L = Leucine | W = Tryptophan | and X represents APSG or a direct bond between M and K.

2. A sequence according to claim 1 which has the formula

5'  ATG—GCT—CCA—TCT—GGC—AAA—TCC—ACG—CTG
    CTT—CTC—TTA—TTT—CTG—CTC—CTG—TGC—CTG
    CCC—TCT—TGG—AAC—GCC—GGC—GCT         3'.

3. A sequence according to claim 1 which has the formula

5'  ATG—AAA—TCC—ACG—CTG—CTT—CTC—TTA—TTT—CTG
    CTC—CTG—TGC—CTG—CCC—TCT—TGG—AAC—GCC—GGC—
    GCT         3'.

4. An expression vector for Gram-negative bacteria, comprising a DNA sequence coding for a precursor of a polypeptide capable of being secreted into the periplasmic space of said bacteria, said precursor being a mature polypeptide extended at its N-terminal end by a signal peptide, wherein the portion of said DNA sequence which codes for said signal peptide is a sequence according to claim 1.

5. A gram-negative bacterium which is transformed by a vector according to claim 4.

6. A bacterium according to claim 5 which belongs to the species *Escherichia coli*.

7. A bacterium according to claim 6 whose chromosomal DNA comprises a cya mutation by deletion and a crp mutation by deletion.

8. A bacterium according to claim 5 or claim 6 wherein the polypeptide is a natural form or a variant in amino acid sequence of hirudin.

9. A bacterium according to claim 8, wherein the hirudin variant is (Lys$^{47}$) HV2.

10. A bacterium, according to claim 5, wherein the polypeptide is human growth hormone.

* * * * *